United States Patent [19]

Rancani

[11] Patent Number: 5,054,518

[45] Date of Patent: Oct. 8, 1991

[54] VARIABLE FLOW SELF-CLEANING VALVE PREFERABLY FOR VENTRICULAR OFFTAKE BRANCHES OF CEPHALORACHIDIAN FLUID

[76] Inventor: Claudio Rancani, Via Col. G. Fincato, 55, Verona, Italy

[21] Appl. No.: 559,172

[22] Filed: Jul. 27, 1990

[30] Foreign Application Priority Data

Aug. 4, 1989 [IT] Italy .................. 84971 A/89

[51] Int. Cl.⁵ ........................................... F16K 15/02
[52] U.S. Cl. ............................... 137/516.27; 137/538
[58] Field of Search .............. 137/516.25, 516.27, 137/538

[56] References Cited

U.S. PATENT DOCUMENTS

| 764,642 | 7/1904 | Stenwall | 137/538 |
|---|---|---|---|
| 1,292,613 | 1/1919 | Kessler | 137/538 |
| 2,005,813 | 6/1935 | Thorsen | 137/538 X |
| 2,977,804 | 4/1961 | Scholin | 137/538 |
| 3,092,133 | 6/1963 | Clark | 137/538 X |
| 3,122,162 | 2/1964 | Sands | 137/516.25 X |
| 3,366,138 | 1/1968 | Graham | 137/538 |
| 3,752,183 | 8/1973 | Griswold | 137/504 |
| 4,675,003 | 6/1987 | Hooven | 137/539 X |
| 4,682,625 | 7/1987 | Christopher | 137/538 |

FOREIGN PATENT DOCUMENTS

| 46-42265 | 12/1971 | Japan | 137/538 |
|---|---|---|---|
| 496445 | 9/1975 | Switzerland . | |

Primary Examiner—John Rivell
Attorney, Agent, or Firm—Notaro & Michalos

[57] ABSTRACT

The present valve, employable by persons affected by hydrocephalus, permits discharge into suitable offtake branches of the excess cephalorhachidian fluid existing in the ventricles of the brain. The valve basically consists of a hollow cylindrical body (1) having inside a seat (5) with an enlarging triangular shape designed to interact with an aptly-shaped capsule or small piston (6) and placed against an antagonist spring (7). This pattern permits to offset the varying amounts of ventricular fluid pressures, discharging outside any fluid, whether large or small, through suitable offtake branches and at the same time it accomplishes a self-cleaning function which ensures a constant flow efficiency.

10 Claims, 1 Drawing Sheet

VARIABLE FLOW SELF-CLEANING VALVE PREFERABLY FOR VENTRICULAR OFFTAKE BRANCHES OF CEPHALORACHIDIAN FLUID

FIELD AND BACKGROUND OF THE INVENTION

The object of the present invention patent is a variable flow valve, preferably applicable in offtake branches for ejection of surplus cephalorhachidian fluid existing in the ventricles of the brain in patients affected by hydrocephalus.

As is known by medical pathology this type of disease is characterized by an increase in the pressure of the cephalorhachidian fluid existing in the ventricles of the brain. This pressure increase is due to a pathological occlusion of the natural paths that permit regulation of this pressure. In these cases it is essential to surgically intervene to form auxiliary channels for the surplus fluid, otherwise the brain will suffer severe and irreparable injuries.

Naturally these offtake branches must be maintained functionally in place by the patient because of the cyclic nature of this abnormal phenomenon, therefore it becomes necessary to use a valve for regulation of ventricular pressure.

In this regard modern surgical engineering has only an extremely limited number of valves to offer. The most well known and used of them is the diaphragm valve, but this valve is subject to a number of flow and tension problems.

This valve, in fact, is manufactured case by case and set for a specific limit pressure that can differ from one patient to another.

This means that increases in ventricular pressure that stay below this limit cannot be discharged. This results in a period of brain suffering that can only be relieved when the pressure exceeds the valve threshold setting.

This type of valve is also easily subject to occlusions and other similar troubles that quickly make the appliance unserviceable.

Other by-pass means have also been developed, such as constant flow systems which are efficient for small pressure variations but which are absolutely inadequate for strong jumps in pressure which require immediate and abundant external discharge.

SUMMARY OF THE INVENTION

The main purpose of the present invention is the development of a valve capable of offsetting increases in ventricle fluid pressure of any size by variable flow ejection, thus eliminating all the problems encountered by the state of the art.

As part of this general scope the valve that forms the object of the present invention specifically evidences a capacity to maintain its own functional efficiency over long time periods thanks to a constant self-cleaning action caused by suitably shaped movable components.

The present valve can be used to offset slight increases in ventricular pressure. It can also, through intermediate channels, offset strong increases in this pressure with immediate and abundant discharge outside.

Another advantage offered by the present invention is that this valve eliminates completely the so-called siphon effect. This because any force applied by the fluid but not caused by ventricular bodies immediately causes blockage of the valve element.

The reliable efficiency and functional merits of the invention, and the simplicity with which it can be produced, are the prerequisites for quick and widespread diffusion of the same even on a large scale.

The invention, in fact, refers to a self-cleaning variable flow valve for offtake channels of ventricular cephalorhachidian fluid characterized by the fact that it consists of a hollow cylindrical body with inlet and outlet openings whose inner wall has a longitudinally extended flared or tapered profile; this cylindrical body internally interacts with a sliding capsule or small piston fitted up against the narrower part of said flared seat by an antagonist spring. This small piston has an annular groove and a linking channel between the groove itself and the end of the piston directed towards the discharge section. This is designed so that all movements by the small piston correspond to a variable flow capacity according to the different amounts of pressure being applied.

BRIEF DESCRIPTION OF THE DRAWINGS

The invention can be better understood from the following description, as well as from the enclosed drawings where.

DESCRIPTION OF THE PREFERRED EMBODIMENT

Figure 1:
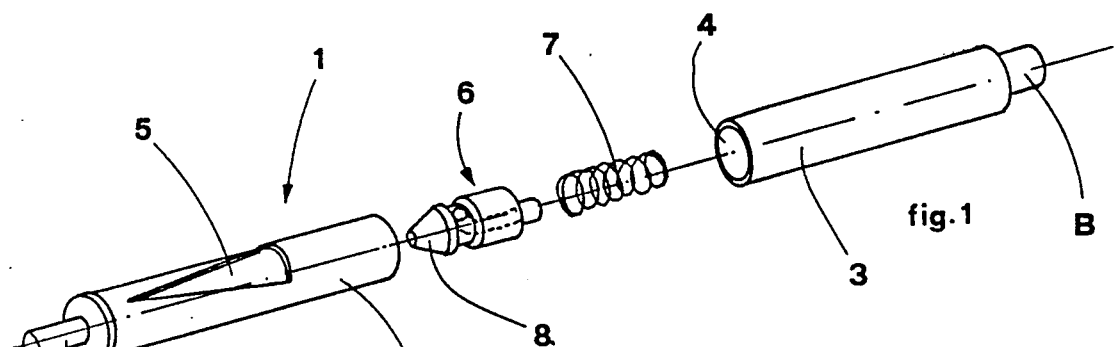
FIG. 1 is a schematic exploded view of a type of valve according to the invention with an assembled cylinder.
Figure 2:
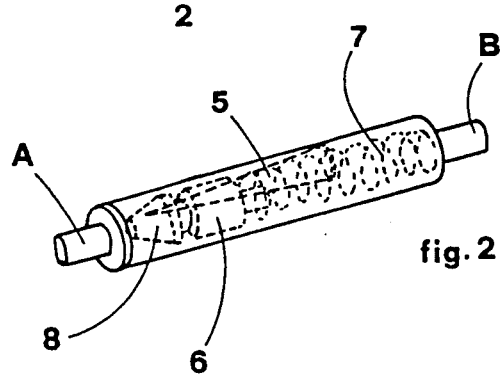
FIG. 2 is a schematic view of the assembled parts with the small piston in its semi-closed position.

With reference to the enclosed illustrations, a cylindrical valve body 1 can, as a whole, be made as one block of material but, for convenience, is obtained in two parts, 2 and 3, where the first part enters completely into the second.

Cylindrical section 2, contrary to part 3, which is hollow and has an opening 4 for insertion of cylinder 2, includes a characteristic carved part or recess 5 or a basically tapered or flared opening in the direction shown in the illustration. Recess 5, when cylindrical body 2 is inserted into body 3, forms a closed internal seat serving the purposes we shall illustrate in the following.

Figure 3:
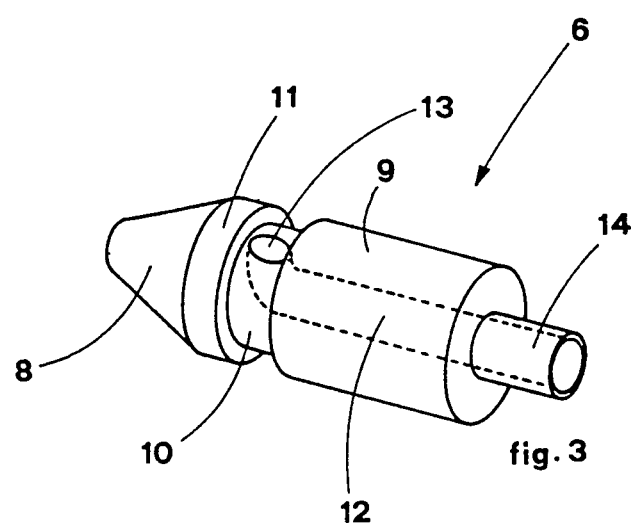
FIG. 3 is a detailed view of the sliding piston.

Cylindrical body 1 houses small movable piston 6 and spring 7 which acts as an antagonist device for the small piston itself, which is pushed towards opening A on the cylindrical body. Opening A is connected, in the case in question, to an offtake branch, not illustrated, coming from the ventricular body subject to pathological pressure increases. B is used to indicate the exit section connected to a drainage channel. Small piston 6 basically consists of a front tapered section 8 (see FIG. 3) acting on an eventual flared profile 8' of opening A and a cylindrical body 9 that forms a seal strip or ring 11 and is interrupted by annular groove 10. Inside channel 12, with port 13 and exit from the rear part of the small piston near a small drain cylinder 14, starts out from groove 10.

Figure 4:
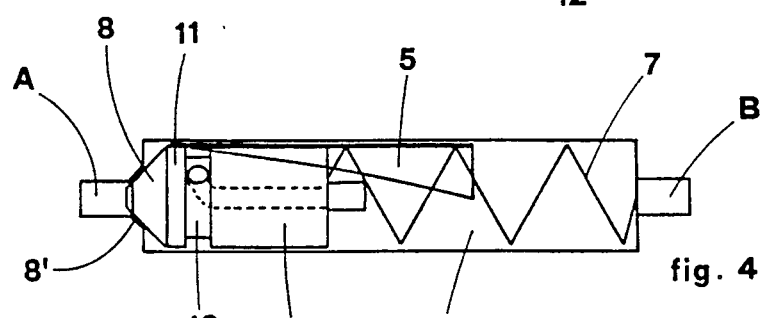
FIGS. 4 and 5 are, respectively, schematic cut-away views of the valve in its closed position and in its maximum capacity open position.

The assembled valve can be seen as illustrated in FIG. 4 with small piston 6 completely pushed by spring 7 towards flared profile 8' which is internally closed off by the tapered section 8 of same. In this phase the cephalorhachidian fluid is at normal pressures and consequently the small piston is not exposed to any force except that of pre-set spring 7. A slight increase in pressure applied by the fluid in opening A will cause small piston 6 to start slowly retracting until seal strip 11 crosses the vertex of tapered recess 5. This permits the fluid to penetrate into annular groove 10 and move from here into channel 12. This channel leads directly into cylinder chamber 15 going towards exit B. If pressure continues to increase the small piston moves further back, permitting an increase in flow rate due to the increase in discharge space provided by flared recess 5.

Figure 5:
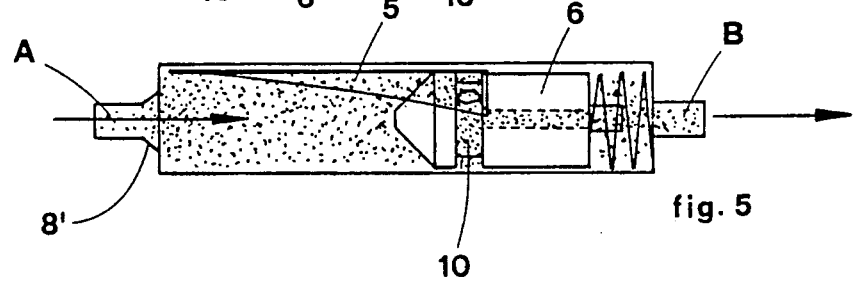

A further increase in fluid pressure will bring the piston to its all-back position as illustrated in FIG. 5. In this position the cross section of seat 5 is in its maximum flow rate position with respect to discharge groove 10 and fluid can be expelled at the highest discharge rate.

It is evident that under normal operating conditions the small piston will move to intermediate positions to permit, for example, an almost constant minimum discharge rate.

To do this spring 7 is set to offset all the pressure conditions that can arise, from a minimum pressure, slightly higher than normal, to a maximum level which ensures that a maximum quantity of fluid will be drained off in the least possible time period in order to ensure quick return to normal ventricular pressure.

The period of suffering by the brain is practically nil since the valve has the capacity to drain quantities going from just a few droplets per minute up to several deciliters per minute. The example in question described a type of valve formed of two cylindrical bodies one of which enters entirely into the other, with the inner body having a flared opening. However other forms of embodiment can be made that in any case permit achievement of an internal cylindrical chamber with a seat with a flared or increasing profile.

One of the advantages of this type of valve is that its design inhibits any abnormal movement of the fluid, preventing suction effects, because spring 7, not exposed to pressure or having pressure that pushes towards opening B, keeps the small piston moved towards opening A and consequently checks fluid backflow.

Any further pressure above and beyond maximum pressure caused, for example, by the siphon effect caused by the peritoneal discharge tube, is offset by the small piston itself which moves to its travel limit where seal strip 11 crosses the base edge of the flared recess 5 and stops flow.

In one possible variant small piston 6 can be modified and have helical grooves carved onto cylindrical surface 9 in place of channel 12. This permits the small piston, during its longitudinal movements inside the cylindrical chamber, to make rotary movements about its axis in order to further enhance the self-cleaning action performed by the valve.

Other variants or modifications can be made to the invention in question but which should in any case be considered to be included within the realm of protection claimed by the present invention.

I claim:

1. A self-cleaning variable flow valve for passing ventricular cephalorhachidian fluid which is at any one of a normal pressure, a minimum elevated pressure, a maximum elevated pressure and any pressure between the minimum and maximum elevated pressures, the valve comprising:

a hollow cylindrical body (1) having a front inlet opening (A) for receiving fluid at one end, and a rear outlet opening (B) at an opposite end, said hollow body having an inner cylindrical surface with a tapered recess (5) therein, which tapers outwardly in a direction from said inlet opening toward said outlet opening from a vertex of said tapered recess to a base of said tapered recess, said hollow body containing a profile (8') defining a valve seat adjacent said inlet opening (A);

a piston (6) slidably mounted in said cylindrical body (1), said piston having a forward tapered section (8) engageable with said profile for blocking a flow of fluid into said hollow body through inlet opening, a seal ring (11) to the rear of said tapered section (8), and a cylindrical surface (9) to the rear of said seal ring, said piston having a linking channel (12) extending therein, said linking channel having an inlet port (13) between said seal ring and said cylindrical surface, and an outlet port at a rear end of said piston which communicates with said outlet opening of said cylindrical body, said seal ring being engaged against the inner surface of said cylindrical body and said piston being movable away from the profile so that when said seal ring passes the vertex of said recess, fluid flows through said inlet opening (A) over said seal ring (11) and into said inlet port for discharging fluid from inlet opening to said outlet opening, and, when said seal ring passes the base of said recess, flow of fluid between said inlet and outlet opening is blocked; and biasing means (7) engaged between said cylindrical body and said piston for urging said tapered section (8) into engagement with said profile (8'), said biasing means being selected to have a biasing force which engages said tapered section against said profile under the normal pressure, which permits the piston to move so that the seal ring passes the vertex but is adjacent the vertex at the minimum elevated pressure, which allows the piston to move so that the seal ring is in the recess and adjacent base under the maximum elevated pressure, and which allows the piston to move so that the seal ring passes the base under pressure above the maximum elevated pressure.

2. A valve according to claim 1, wherein said hollow body (1) comprises an outer cylinder (3) having a front open end (4) and carrying said outlet opening (B), and an inner cylinder (2) telescopically engaged into said outer cylinder through said open end of said outer cylinder, said inner cylinder including a tapered opening (5) defining said tapered recess.

3. A valve according to claim 2, wherein said piston includes an annular groove (10) between said seal ring (11) and said cylindrical surface (9), said inlet port (13) opening into said annular groove.

4. A valve according to claim 3, wherein said piston (6) includes a rear drain cylinder (14) having a smaller diameter than said cylindrical surface (9), said outlet port extending through said drain cylinder.

5. A valve according to claim 4, wherein said tapered section (8) and said profile (8') are conical.

6. A valve according to claim 5, wherein said biasing means comprises a spring (7).

7. A valve according to claim 1, wherein said piston includes an annular groove (10) between said seal ring (11) and said cylindrical surface (9), said inlet port (13) opening into said annular groove.

8. A valve according to claim 1, wherein said piston (6) includes a rear drain cylinder (14) having a smaller diameter than said cylindrical surface (9), said outlet port extending through said drain cylinder.

9. A valve according to claim 1, wherein said tapered section (8) and said profile (8') are conical.

10. A valve according to claim 1, wherein said biasing means comprises a spring (7).

* * * * *